United States Patent
Korthoff et al.

[11] Patent Number: 5,139,514
[45] Date of Patent: Aug. 18, 1992

[54] COMBINED NEEDLE-SUTURE DEVICE
[75] Inventors: Herbert W. Korthoff, Westport; Richard N. Granger, Huntington, both of Conn.
[73] Assignee: United States Surgical Corporation, Norwalk, Conn.
[21] Appl. No.: 771,533
[22] Filed: Oct. 7, 1991

Related U.S. Application Data
[63] Continuation of Ser. No. 532,928, Jun. 4, 1990, abandoned, which is a continuation-in-part of Ser. No. 413,240, Sep. 27, 1989.
[51] Int. Cl.$^5$ ............................................. A61B 17/00
[52] U.S. Cl. ..................... 606/224; 606/223
[58] Field of Search ............................. 606/223–227

[56] References Cited

U.S. PATENT DOCUMENTS

| | | |
|---|---|---|
| 86,769 | 2/1869 | Marriott . |
| 295,612 | 3/1884 | Bailey . |
| 299,305 | 5/1884 | Weed . |
| 877,476 | 1/1908 | Bach . |
| 1,106,667 | 8/1914 | Minahan . |
| 1,250,114 | 12/1917 | Bigelow et al. . |
| 1,558,037 | 10/1925 | Morton . |
| 1,591,021 | 7/1926 | Davis . |
| 1,613,206 | 1/1927 | Souttar ............................ 606/226 |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. ..................... 606/226 |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,928,395 | 3/1960 | Forbes et al. . |
| 3,311,110 | 3/1967 | Singerman et al. . |
| 3,394,704 | 7/1968 | Dery . |
| 3,416,534 | 12/1968 | Quinn . |
| 3,799,169 | 3/1974 | Beroff et al. . |
| 3,835,912 | 9/1974 | Kristensen et al. . |
| 3,875,946 | 4/1975 | Duncan .......................... 606/227 |
| 3,877,570 | 4/1975 | Barry ............................. 206/63.3 |
| 3,880,167 | 4/1975 | Hardwick . |
| 3,890,975 | 6/1975 | McGregor . |
| 3,910,282 | 10/1975 | Messer et al. . |
| 3,918,455 | 11/1975 | Coplan ........................... 606/225 |
| 3,924,630 | 12/1975 | Walldorg . |
| 3,926,194 | 12/1975 | Greenberg et al. . |
| 3,943,933 | 3/1976 | Gertzman . |
| 3,949,756 | 4/1976 | Ace . |
| 3,963,031 | 6/1976 | Hunter ........................... 606/227 |
| 3,980,177 | 9/1976 | McGregor ...................... 606/227 |
| 3,981,307 | 9/1976 | Borysko . |
| 4,054,144 | 10/1977 | Hoffman et al. . |
| 4,072,041 | 2/1978 | Hoffman et al. . |
| 4,124,027 | 11/1978 | Boss . |
| 4,127,133 | 11/1978 | Martinez . |
| 4,169,477 | 10/1979 | Bokros . |
| 4,359,053 | 11/1982 | Benjamin . |
| 4,411,654 | 10/1983 | Boarini et al. ................. 604/165 |
| 4,596,728 | 6/1986 | Yang et al. ..................... 606/151 |
| 4,624,879 | 11/1986 | Van Dijck et al. . |
| 4,672,734 | 6/1987 | Kawada et al. . |
| 4,792,336 | 12/1988 | Hlavaceh et al. .............. 623/13 |
| 4,805,292 | 2/1989 | Noguchi ......................... 29/445 |
| 4,926,860 | 5/1990 | Stice et al. . |

FOREIGN PATENT DOCUMENTS

| | | |
|---|---|---|
| 3223153 | 8/1983 | Fed. Rep. of Germany . |
| 9101152.3 | 5/1991 | Fed. Rep. of Germany . |
| 2268534 | 11/1975 | France . |
| 512237 | 10/1971 | Switzerland . |

OTHER PUBLICATIONS
Raychem Corporation Product specification RT-850 for Thermofit TM Kynar Tubing dated Mar. 6, 1984.

*Primary Examiner*—Stephen C. Pellegrino
*Assistant Examiner*—Gary Jackson
*Attorney, Agent, or Firm*—Thomas R. Bremer; Peter G. Dilworth; Rocco S. Barrese

[57] ABSTRACT

A suture is attached to a surgical needle possessing a shank of reduced diameter the butt end of which is rounded. Attachment is accomplished by means of a shrinkable tubing which is fitted about the shank of the needle and an end of the suture, application of heat to the tubing effecting its shrinkage with consequent secure attachment of the needle to the suture. Rounding of the butt end of the needle shank minimizes the possibility that during use, the needle will protrude or rip through the tubing or otherwise compromise the security of the attachment of the needle to the suture.

47 Claims, 3 Drawing Sheets

COMBINED NEEDLE-SUTURE DEVICE

CROSS REFERENCE TO RELATED APPLICATION

This is a continuation of copending application Ser. No. 07/532,928 filed on Jun. 4, 1990, now abandoned which is a continuation in part of commonly assigned, copending U.S. patent application Ser. No. 413,240, filed Sep. 27, 1989, now pending.

BACKGROUND OF THE INVENTION

The present invention relates to a combined surgical needle-suture device, and, more particularly, to such a device in which a shrinkable tubing attaches a suture to a surgical needle.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the U.S. Pharmacopeia (USP). The USP prescribes minimum individual pull-out forces and minimum average pull-out forces as measured for five needle-suture combinations. The minimum pull-out forces for both standard and removable needle-suture attachment set forth in the USP are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031), and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g. by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle siliconization process. Safeguards employed in an attempt to prevent the introduction of such foreign materials, e.g., water blocking during needle silconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

Commonly assigned, copending U.S. patent application Ser. No. 413,240, filed Sep. 27, 1989, describes a combined surgical needle-suture device and surgical needle-suture attachment method which overcomes the aforementioned drawbacks of the previously known needle-suture combinations and needle-suture attachment methods. In accordance with said application, a combined needle-suture device is provided in which a surgical needle having a shank of reduced cross-section is attached to a suture through a shrinkable tubing, or micro-ferrule, which is fitted about the needle shank and a portion of the suture. Application of energy to the shrinkable tubing brings the tubing into engagement with both the needle shank and the suture. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

SUMMARY OF THE INVENTION

It has now been found that by rounding the butt end of the reduced diameter shank of the combined surgical needle-suture device of aforementioned Ser. No. 413,240, a surgeon can more readily "turn corners" and/or flex the butt end of the shank during the suturing procedure without incurring a risk that the butt end of the shank will protrude through or rip the attached tubing or otherwise compromise the security of the needle-suture attachment.

In accordance with the present invention, there is provided a combined surgical needle-suture device which comprises:
 a) a needle having a shank of reduced cross-section, the butt end of the shank being rounded;
 b) a suture; and,
 c) a shrinkable tubing around said needle shank and a portion of said suture.

Further, in accordance with this invention, there is provided a method for attaching a surgical needle to a suture to provide a combined surgical needle-suture device which comprises:
 a) providing a needle having a shank end of reduced cross-section, the butt end of the shank being rounded;
 b) placing a shrinkable tubing around the reduced diameter shank and the suture; and,
 c) applying energy to the shrinkable tubing to bring the tubing into engagement with the needle shank and suture.

When the suture is made to bear under tension at a relatively sharp angle against its attached needle which, of course, would tend to occur when turning corners during suturing, the rounded surface of the butt end of the needle shank prevents the shank from deforming or, in an extreme case, from penetrating through, the tubing which secures the suture and needle to each other. Accordingly, providing the butt end of the shank with rounded corners or edges enhances the security and reliability of the needle-suture attachment and diminishes the possibility of premature, unintended detachment of the needle from its suture during a suturing procedure.

BRIEF DESCRIPTION OF THE DRAWINGS

The present invention will become more apparent from the following detailed description taken in conjunction with the accompanying drawings in which.

DETAILED DESCRIPTION OF THE INVENTION

The present invention relates to a combined surgical needle-suture device and surgical needle-suture attachment method. The invention has application to any suture material whether absorbable or non-absorbable, natural or synthetic, braided or monofilament, and to any needle material and configuration whether straight or curved. The invention may be used to effect standard or detachable needle attachment as described in more detail below.

Figure 1:
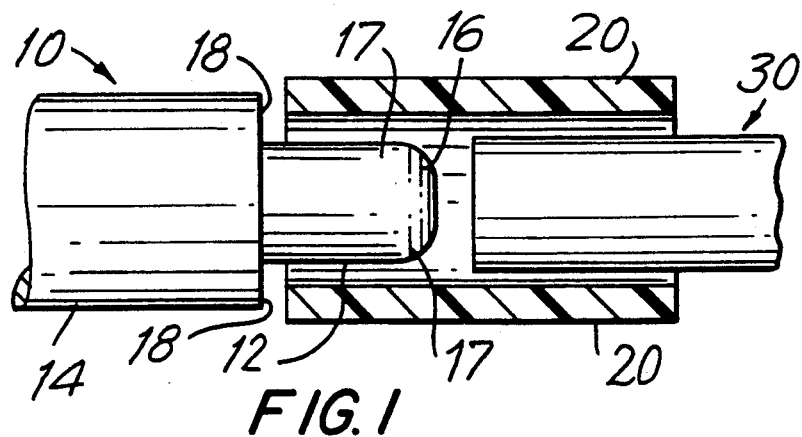
FIG. 1 is a side cross-sectional view of a needle and a suture with a tubing positioned therearound (prior to engagement of the tubing with the needle and suture)
Figure 2:
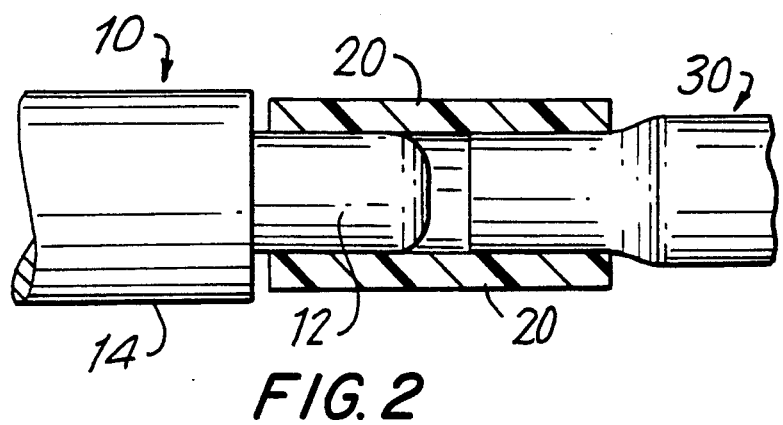
FIG. 2 is a side cross-sectional view of the tubing of FIG. 1 in engagement with the needle and suture.
Figure 3:
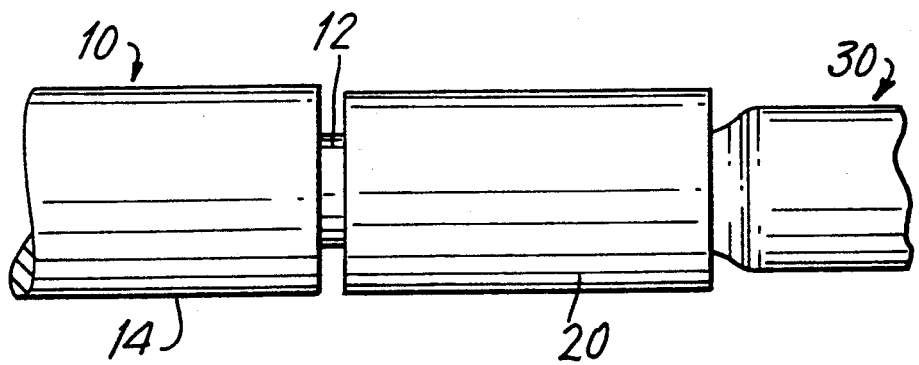
FIG. 3 is a side view of a needle-suture attachment of the present invention.
Figure 4:
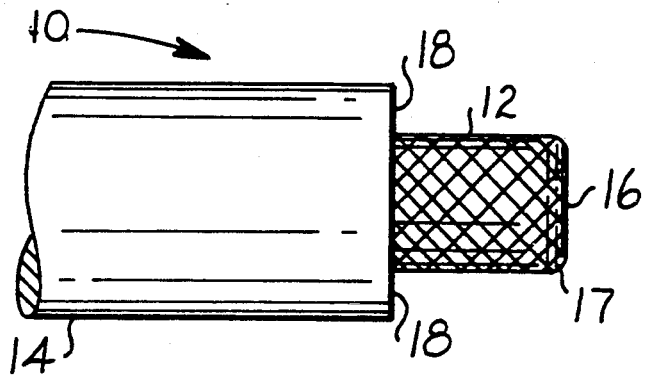
FIG. 4 is a side view of an alternative embodiment of the present invention in which a shank of the needle is scored.
Figure 5:
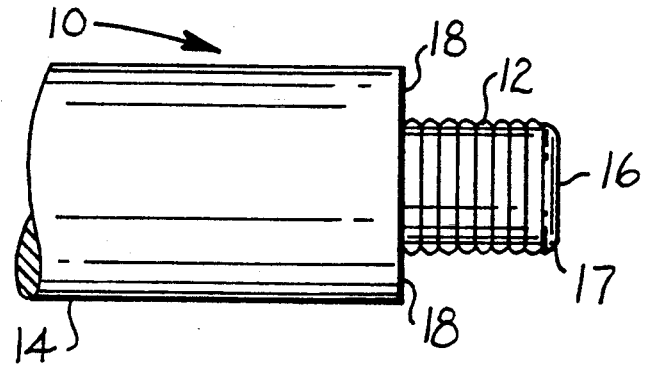
FIG. 5 is a side view of an alternative embodiment of the present invention in which the needle shank is ribbed.
Figure 6:
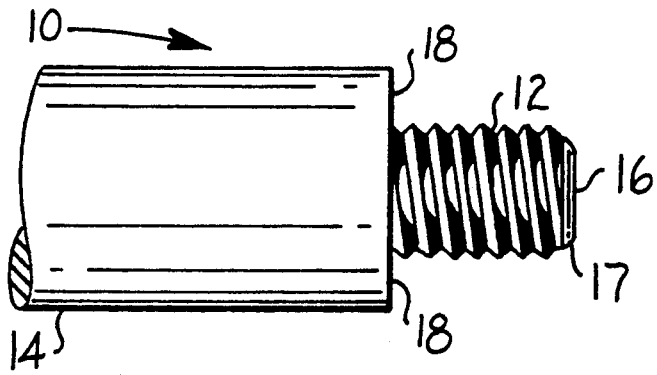
FIG. 6 is a side view of an alternative embodiment of the present invention in which the needle shank is threaded.
Figure 7:
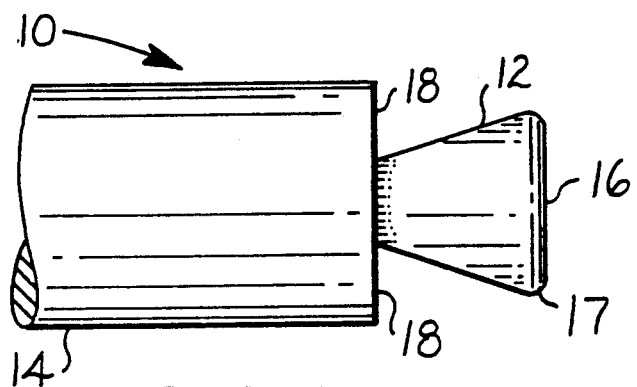
FIG. 7 is a side view of an alternative embodiment of the present invention in which the needle shank is tapered to expand in a direction away from a remainder of the needle.
Figure 8:
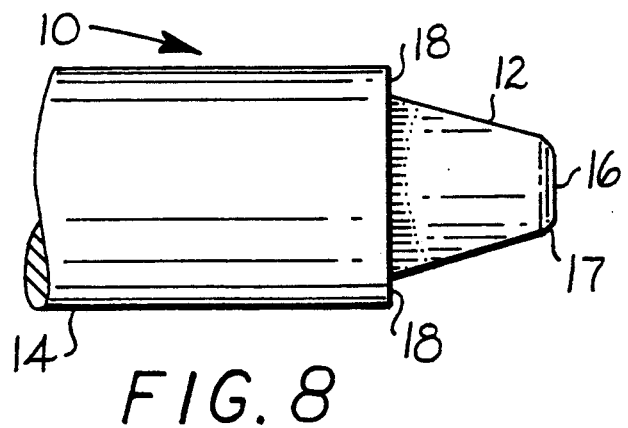
FIG. 8 is a side view of an alternative embodiment of the present invention in which the needle shank is tapered to expand in a direction towards the remainder of the needle.

Referring to FIGS. 1-3, needle 10 has a reduced cross-sectional diameter at its shank end 12 relative to the remaining portion 14 of the needle. The diameter of shank end 12 may be reduced by any conventional means, e.g., by turning on a lathe. Typically, shank end 12 has a diameter from 10 to 65% smaller than the remainder of the needle 14, and preferably from 25 to 50% smaller. It is also possible to provide shank end 12 with a texturized surface to facilitate gripping by shrinkable tubing 20. For example, shank end 12 may be scored, ribbed or threaded, in whole or in part (FIGS. 4-6 respectively). It may also be desirable to taper shank end 12 such that its butt, or distal end 16 is of greater cross-sectional diameter than the cross-sectional diameter of shank end 12 in the region of shoulder 18, or vice versa (FIGS. 7 and 8 respectively).

Butt end 16 possesses rounded, beveled or chamfered force-distributing corners, or edges, 17 which serve to prevent shank end 12 from protruding through or ripping shrinkable tubing 20 in the attached configuration of the combined surgical needle-suture device as illustrated in FIG. 2. Bevelling or chamfering of the edges of butt end 16, while marginally less effective than rounding, are to be considered equivalent to the latter for the purpose of this invention. Accordingly, as used herein, the terms "rounding" and "rounded" shall be taken as essentially equivalent to "beveling", "beveled", "chamfering" and "chamfered". As the radius of curvature of rounded corners 17 increases to some maximum value, e.g., that of the radius of butt end 16 when in cross section the butt end defines a circle, curved corners 17 will approach a hemispherical shape which maximizes the distribution of the force with which tubing 20 is made to bear against the edges of shank 12 when the suture is brought under tension against its attached needle at some sharp angle. However, even with a radius of curvature which is less than the maximum achievable for a particular needle shank, e.g., 20-50% of the maximum radius of curvature, rounded corners 17 will still tend to prevent excessive distortion of, or damage to, tubing 20 although possibly with less effectiveness in this regard.

Rounding, beveling or chamfering of the butt end 16 of shank 12 to provide force-distributing corners 17 can be accomplished by any of a variety of conventional machining techniques, e.g., grinding, lathing, tumbling, etc.

Suture 30 is also positioned within shrinkable tubing 20. A gap may exist between shank end 12 and suture 30 (as shown in FIGS. 1 and 2) or shank end 12 may abut against suture 30. As shown in FIG. 1, suture 30 may initially be of uniform cross-section throughout its length. Alternatively, the tip region of suture 30, i.e., the region inserted into tubing 20, may be of reduced cross-section relative to the remainder of suture 30, e.g., by tipping the suture tip with an adhesive or resinous tipping agent while suture 30 is under tension. (See, e.g., Canadian Patent No. 1,009,532.) Resin tipping may be desirable to prevent brooming of the suture, particularly for multifilament braided sutures, by rigidifying the end of the suture to facilitate its handling during the attachment process. Reducing the diameter of the suture tip, as by tipping under tension, may be desirable to allow a suture of larger diameter, e.g., a suture diameter equal to the diameter of the needle to which it is to be attached, to be more efficiently attached to the needle using the shrinkable tubing of the present invention. It is not necessary according to the present invention, however, to reduce the diameter of the tip region of suture 30 to efficiently attach needle 10 to suture 30. Indeed, it may be possible or desirable to apply a tipping agent to prevent brooming without reducing suture diameter. As shown in FIG. 1, shrinkable tubing 20 initially has an inner diameter that is larger than the outer diameter of the tip region of suture 30, thereby minimizing the importance of suture tipping.

After shrinkable tubing 20 is placed around shank end 12 of needle 10 and the tip region of suture 30, energy is applied to tubing 20. In response to this energy, tubing 20 contracts or shrinks and engages shank end 12 and suture 30. The overall length of tubing 20 may also be affected by the application of energy, e.g., the length of tubing 20 may reduce. Thus, the shrinking of tubing 20 brings the inner surface of tubing 20 into engagement with shank end 12 and suture 30, thereby securing suture 30 to needle 10. Suitable energy sources include heat (convective or conductive), radiation, microwave energy, laser energy, etc.

As shown in FIGS. 1-2, shrinkable tubing 20 is simultaneously placed around both suture 30 and shank end 12 of needle 10 in one embodiment of the present invention. It is preferable, however, to sequentially secure tubing 20 to needle 10 and suture 30. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, suture 30 is inserted into tubing 20 and additional energy is applied thereto. Sequential shrinkage of tubing 20 makes it possible to vary the amount of energy used in securing tubing 20 to shank end 12 and suture 30, respectively, and to limit the exposure of suture 30 to energy during the attachment process. It may also be desirable to cool suture 30 in the region outside tubing 20 to prevent any undesirable degradation thereof, e.g., with a cold air curtain.

As shown in FIGS. 2 and 3, the shrinkage of tubing 20 typically compresses suture 30 to some extent. This is particularly true where the suture is a braided, multifilament material having void spaces in its structure. For example, tubing 20 may compress suture 30 by as much as 30 to 35% for a braided, synthetic absorbable suture and by a minimal amount for a relatively stiff material such as a monofilament surgical gut.

Shrinkable tubing 20 may be manufactured from any material which shrinks, i.e., reduces in diameter, in response to the application of energy. Suitable materials include shrinkable plastic materials, such as polyvinylidene fluoride materials available from Raychem Corporation, Menlo Park, Calif., under the tradename Kynar. Other kinds of shrinkable plastic tubing, e.g., those based on the known types of shape-recoverable polyethylene resins, can also be used herein with good results.

The shrinkable tubing is typically extruded such that the inner diameter is less than the final desired inner diameter, i.e., the inner diameter of the tubing after energy application in the attachment method of the present invention. Thereafter, the extruded tubing is expanded radially outward through radial expansion means to provide a tubing of expanded inner diameter as shown, for example, by tubing 20 in FIG. 1. Such plastic tubing is thus adapted to shrink or "recover" to its original extruded inner diameter in response to the application of a predetermined amount of energy.

The amount of energy applied to the tubing to effect the desired attachment, i.e., diameter reduction, depends upon the chemical characteristics of the tubing material, the relative dimensions of the tubing, the shank end of the needle and the suture, and the desired pull-out force for the needle-suture combination. For example, one polyvinylidene fluoride material available from Raychem Corporation (TT-850) shrinks at temperatures greater than 175° C., and is adapted to recover to about 50% of its radially expanded inner diameter. In such case, tubing 20 may be brought into engagement with shank end 12 of needle 10 and suture 30, either simultaneously or sequentially, by heating tubing 20 to a temperature above 175° C. Tubing 20 may be heated through contact with a hot gas stream or with heated dies, or by other heating means. Typically, the outer diameters of shank end 12 and suture 30 (in the region inserted into tubing 20) are greater than the fully recovered diameter of tubing 20, e.g., greater than 50% of the initial inner diameter of tubing 20 for the RT-850 material, such that tubing 20 engages shank end 12 and suture 30. This engagement provides the needle-suture combination of the present invention.

As noted above, the attachment method of the present invention may be easily used to effect both standard needle attachment and detachable needle attachment. Preferably, the pull-out force of a given needle-suture combination is controlled through control of the energy source. Thus, using the identical inventories of needles, sutures and tubings, it is possible to produce either standard or detachable needle products through simple energy variations. In the case of detachable needle attachment, it is preferred that the attachment conditions be controlled such that the tubing remains secured to the needle once the suture is detached.

The needle-suture attachment method of the present invention has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies). These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method of the present invention is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may also be recovered and reused, thereby greatly reducing processing waste. The range of acceptable suture diameters is greatly expanded due to the ability of the tubing to recover or shrink to varying degrees, thereby minimizing the likelihood that suture production will be rejected for inability to attach several needle sizes because the shrinkable tubing is capable of recovering or shrinking to varying degrees. This greatly simplifies inventory considerations.

Needle-suture combinations produced according to the present invention are atraumatic and advantageously exhibit flexibility in the attachment region. Both standard needle attachment and detachable needle attachment products may be produced with great processing ease.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A combined surgical needle-suture device which comprises:
    a) a needle having a shank of reduced cross-section, the butt end of the shank being rounded;
    b) a suture; and,
    c) a shrinkable tubing around said needle shank and a portion of said suture to couple the same without swaging or crimping.

2. The combined surgical needle-suture device of claim 1 wherein the cross-section of the butt end of the needle defines a circle and the radius of curvature of the rounded section of the shank is substantially that of the radius of said circle.

3. The combined surgical needle-suture device of claim 2 wherein the radius of curvature of the rounded section of the shank is at least about 50% of the radius of the circle.

4. The combined surgical needle-suture device of claim 2 wherein the radius of curvature of the rounded section of the shank is at least about 20% of the radius of the circle.

5. The combined surgical needle-suture device of claim 1 wherein said suture is a non-absorbable material selected from the group consisting of silk, nylon, polyester, polypropylene, linen and cotton.

6. The combined surgical needle-suture device of claim 5 wherein said suture is a braided multifilament.

7. The combined surgical needle-suture device of claim 1 wherein said suture is an absorbable material selected from the group consisting of catgut and synthetic materials including polymers and copolymers of glycolic and lactic acids.

8. The combined surgical needle-suture device of claim 7 wherein said suture is a braided multifilament.

9. The combined surgical needle-suture device of claim 1 wherein said suture portion is tipped with an adhesive or resinous coating.

10. The combined surgical needle-suture device of claim 9 wherein said suture portion is of reduced cross-section as compared to the remainder of the suture.

11. The combined surgical needle-suture device of claim 1 wherein said shrinkable tubing is manufactured from a shrinkable plastic material.

12. The combined surgical needle-suture device of claim 11 wherein said shrinkable plastic material is a polyvinylidene fluoride or polyethylene material.

13. The combined surgical needle-suture device of claim 1 wherein said shrinkable tubing is color-coded to correspond to the suture material.

14. The combined surgical needle-suture device of claim 1 wherein the pull-out force for said device is as defined for standard needle attachment.

15. The combined surgical needle-suture device of claim 1 wherein in the pull-out force for said device is as defined for removable or detachable needle attachment.

16. The combined surgical needle-suture device of claim 1 wherein said device is atraumatic.

17. The combined surgical needle-suture device of claim 1 wherein said device is flexible in the region of said shrinkable tubing.

18. The combined surgical needle-suture device of claim 1 wherein said reduced diameter shank is texturized.

19. The combined surgical needle-suture device of claim 18 wherein said shank is ribbed, scored or tapered, in whole or in part.

20. The combined surgical needle-suture device of claim 1 wherein said reduced diameter shank and said suture portion abut within said shrinkable tubing.

21. The combined surgical needle-suture device of claim 1 wherein said shrinkable tubing compresses said suture portion.

22. The combined surgical needle-suture device of claim 21 wherein said tubing compresses said suture portion by as much as 35%.

23. The combined surgical needle-suture device of claim 1 wherein said shank of reduced cross-section has a diameter that is 35% to 90% the diameter of said needle.

24. The combined surgical needle-suture device of claim 1 wherein the shank is provided with a texturized surface to facilitate gripping by said shrinkable tubing.

25. The combined surgical needle-suture device of claim 24, wherein the shank is scored, ribbed or threaded in whole or in part.

26. The combined surgical needle-suture device of claim 1, wherein the shank of reduced cross-section forms a shoulder with a remainder of said needle.

27. The combined surgical needle-suture device of claim 26, wherein said shank is tapered in a direction toward said shoulder, such that a distal end of said shank is of greater cross-sectional diameter than cross-sectional diameter of said shank in a region of said shoulder.

28. The combined surgical needle-suture device of claim 26, wherein said shank is tapered in a direction away from said shoulder, such that a distal end of said shank is of smaller cross-sectional diameter than cross-sectional diameter of said shank in a region of said shoulder.

29. A method for attaching a surgical needle to a suture comprising:
 a) providing a needle having a shank of reduced cross-section, the butt end of the shank being rounded;
 b) placing a shrinkable tubing around the reduced diameter needle shank and the suture; and,
 c) applying energy to the shrinkable tubing to bring the tubing into engagement with the needle shank and the suture.

30. The method of claim 29 wherein the cross-section of the butt end of the needle defines a circle and the radius of curvature of the rounded section of the shank is substantially that of the radius of said circle.

31. The method of claim 30 wherein the radius of curvature of the rounded section of the shank is at least about 50% of the radius of the circle.

32. The method of claim 30 wherein the radius of curvature of the rounded section of the shank is at least about 20% of the radius of the circle.

33. The method of claim 29 said needle is manufactured from a material selected from the group consisting of Series 300 stainless steels, Series 400 stainless steels and MP35N.

34. The method of claim 29 wherein said reduced diameter shank is produced by machining said needle.

35. The method of claim 29 wherein said shank is texturized.

36. The method of claim 35 wherein said shank is ribbed, scored or tapered, in whole or in part.

37. The method of claim 29 wherein said shrinkable tubing is manufactured from a shrinkable plastic material.

38. The method of claim 37 wherein said shrinkable plastic material is a polyvinylidene fluoride or polyethylene material.

39. The method of claim 29 wherein said shrinkable tubing is adapted to shrink to an inner diameter as low as 50% of its original inner diameter when placed on the needle shank and suture.

40. The method of claim 29 wherein said shrinkable tubing is placed over the tip region of said suture and said tip region is tipped with an adhesive or resinous coating.

41. The method of claim 40 wherein said tipped region is of reduced cross-section as compared to the untipped region of said suture.

42. The method of claim 29 wherein said applied energy is convective or conductive heat, radiation or microwave energy.

43. The method of claim 29 wherein said energy application is controlled to produce a needle that is detachably attached to said suture.

44. The method of claim 29 wherein said shrinkable tubing is sequentially placed around the needle shank and the suture and wherein energy is applied to the shrinkable tubing after each sequential placement.

45. The method of claim 44 wherein said shrinkable tubing is first placed around said needle shank.

46. The method of claim 29 wherein said shrinkable tubing compresses said suture upon engagement therewith.

47. The method of claim 46 wherein said shrinkable tubing compresses said suture by as much as 35%.

* * * * *